(12) United States Patent  (10) Patent No.: US 10,238,299 B2
Murakoshi  (45) Date of Patent: Mar. 26, 2019

(54) PHOTOACOUSTIC IMAGE-GENERATING APPARATUS AND LIGHT SOURCE CONTROL METHOD

(71) Applicant: FUJIFILM Corporation, Tokyo (JP)

(72) Inventor: Dai Murakoshi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 370 days.

(21) Appl. No.: 15/001,416

(22) Filed: Jan. 20, 2016

(65) Prior Publication Data

US 2016/0135689 A1  May 19, 2016

Related U.S. Application Data

(63) Continuation of application No. PCT/JP2014/065954, filed on Jun. 17, 2014.

(30) Foreign Application Priority Data

Aug. 2, 2013 (JP) .................................. 2013-161232
Jun. 6, 2014 (JP) .................................. 2014-117396

(51) Int. Cl.
*A61B 5/00* (2006.01)
*A61B 8/00* (2006.01)
*A61B 8/08* (2006.01)

(52) U.S. Cl.
CPC .......... *A61B 5/0095* (2013.01); *A61B 5/0035* (2013.01); *A61B 5/6848* (2013.01);
(Continued)

(58) Field of Classification Search
None
See application file for complete search history.

(56) References Cited

U.S. PATENT DOCUMENTS 5,842,994 A * 12/1998 TenHoff .................. A61B 8/12
  600/466
2004/0131299 A1 * 7/2004 Adoram ............... A61B 8/0833
  385/12

(Continued)

FOREIGN PATENT DOCUMENTS

JP  2008-253482 A  10/2008
JP  2009-31262 A  2/2009

OTHER PUBLICATIONS

International Preliminary Report on Patentabilty and English Translation of the Written Opinion of the International Searching Authority (Forms PCT/IB/373 and PCT/ISA/237), issued in PCT/JP2014/065954, dated Feb. 2, 2016.

(Continued)

*Primary Examiner* — Katherine Fernandez
*Assistant Examiner* — Yi-Shan Yang
(74) *Attorney, Agent, or Firm* — Birch, Stewart, Kolasch & Birch, LLP (57) ABSTRACT

At least a tip portion of a puncture needle 15 is inserted into a subject. The puncture needle 15 includes a light guide member which guides light from a laser unit 13, and a light emission unit which is provided in the vicinity of the tip portion and emits light guided by the light guide member, and generates a photoacoustic wave caused by light from the light emission unit in the tip portion. A probe 11 detects the photoacoustic wave from the puncture needle 15 in a state where the puncture needle 15 is inserted into the subject. A Photoacoustic image generation unit 25 generates a photoacoustic image based on the detected photoacoustic wave. A Light source control unit 30 controls the amount of light emitted from the light emission unit based on the photoacoustic image.

17 Claims, 9 Drawing Sheets

(52) U.S. Cl.
CPC .......... *A61B 8/4416* (2013.01); *A61B 8/0841* (2013.01); *A61B 2576/00* (2013.01)

(56) References Cited

U.S. PATENT DOCUMENTS

| | | | | |
|---|---|---|---|---|
| 2011/0098572 A1* | 4/2011 | Chen | .................... | A61B 5/0062 600/463 |
| 2011/0106478 A1* | 5/2011 | Someda | ............... | A61B 5/0059 702/104 |
| 2012/0029829 A1* | 2/2012 | Li | ........................ | A61B 5/0059 702/19 |
| 2014/0180126 A1* | 6/2014 | Millett | ................. | A61B 8/4494 600/467 |
| 2014/0180268 A1* | 6/2014 | Whiseant | ............. | A61B 5/0084 606/33 |
| 2014/0200438 A1* | 7/2014 | Millett | ................. | A61B 8/0841 600/424 |
| 2014/0357997 A1* | 12/2014 | Hartmann | ................ | A61B 8/12 600/439 |

OTHER PUBLICATIONS

International Search Report, issued in PCT/JP2014/065954, dated Jul. 15, 2014.
Written Opinion of the International Searching Authority, issued in PCT/JP2014/065954, dated Jul. 15, 2014.

\* cited by examiner

PHOTOACOUSTIC IMAGE-GENERATING APPARATUS AND LIGHT SOURCE CONTROL METHOD

CROSS-REFERENCE TO RELATED APPLICATIONS

This application is a Continuation of PCT International Application No. PCT/JP2014/065954 filed on Jun. 17, 2014, which claims priority under 35 U.S.C § 119 (a) to Japanese Patent Application No. 2013-161232 filed on Aug. 2, 2013 and Japanese Patent Application No. 2014-117396 filed on Jun. 6, 2014. Each of the above application(s) is hereby expressly incorporated by reference, in its entirety, into the present application.

BACKGROUND OF THE INVENTION

1. Field of the Invention

The present invention relates to a photoacoustic image-generating apparatus which generates a photoacoustic image based on a photoacoustic wave caused by light irradiation. Also, the present invention relates to a method of controlling a light source in the photoacoustic image-generating apparatus.

2. Description of the Related Art

As a kind of an image inspection method capable of noninvasively inspecting the internal state of a living body, an ultrasonic inspection method is known. In the ultrasonic inspection, an ultrasonic probe which can transmit and receive an ultrasonic wave is used. If an ultrasonic wave is transmitted from the ultrasonic probe to a subject (living body), the ultrasonic wave advances through the inside of the living body and is reflected on a tissue interface. A reflected ultrasonic wave is received using the ultrasonic probe, and a distance is calculated based on the time until the reflected ultrasonic wave is returned to the ultrasonic probe, whereby the stage of the inside can be imaged.

Photoacoustic imaging for imaging the inside of a living body using a photoacoustic effect is known. In general, in photoacoustic imaging, the inside of a living body is irradiated with a pulsed laser light, such as a pulsed laser. In the inside of the living body, a tissue of the living body absorbs energy of the pulsed laser light, and an ultrasonic wave (photoacoustic wave) is generated due to adiabatic expansion caused by the absorbed energy. The photoacoustic wave is detected using an ultrasonic probe or the like, and a photoacoustic image is constituted based on the detection signal, whereby the inside of the living body can be visualized based on the photoacoustic wave.

JP2009-31262A describes a combination of biological information imaging using photoacoustics and treatment using a puncture needle. In JP2009-31262A, a physician or the like observes a photoacoustic image to view a diseased part, such as a tumor, a region suspected of a diseased part, or the like. In order to inspect such a region more accurately, or in order to perform injection or the like in the diseased part, cells are gathered or injection in the diseased part is performed using a puncture needle such as an injection needle or a cytologic needle. In JP2009-31262A, puncturing can be performed while observing the diseased part using the photoacoustic image.

SUMMARY OF THE INVENTION

Normally, light irradiation to the subject is performed from the surface of the subject. In particular, if the tip of the puncture needle is punctured to a deep position, light irradiated from the surface of the subject does not sufficiently reach the puncture needle which has been punctured to the deep position, and it is difficult to recognize the position of the puncture needle in the photoacoustic image. Furthermore, since light is irradiated from the outside of the needle, a photoacoustic wave is generated from the entire needle body as well as from the tip, and the tip of the needle is hardly recognized visually.

For the above-described problem, it is considered that light is guided to the tip of the needle and light irradiation is performed from the tip of the needle. Since the light is guided to the tip of the needle, the light can be irradiated at the tip of the needle even if the tip of the needle is punctured in the subject deeply. For this reason, even if the tip of the needle is punctured to a deep position, compared to the case where light irradiation is performed from the surface of the subject, a photoacoustic wave can be generated. Furthermore, since a photoacoustic wave can be selectively generated at the portion of the tip of the needle, the tip of the needle is easily recognized visually.

However, in the case that the light is guided to the tip of the needle, if the intensity of the light irradiated from the tip of the needle is too weak when the tip of the needle is punctured in the subject deeply, a photoacoustic wave due to light irradiation from the tip of the needle cannot be detected to the sufficient intensity, and the tip of the needle is not easily recognized in a photoacoustic image. On the other hand, if the intense light is irradiated from the tip of the needle while the tip of the needle is punctured in the subject deeply, an intense photoacoustic wave is detected when the tip of the needle is punctured to a shallow position, causing a flare-like artifact or an artifact due to multiple reflections, and visibility of the tip of the needle is degraded. This problem occurs not only when using the puncture needle, but also when the position of the tip of the inserted object which is inserted into the subject is recognized using a photoacoustic image.

An object of the invention is to provide a photoacoustic image-generating apparatus and a light source control method capable of improving visibility of a tip portion of an inserted object when light is guided to the tip portion of the inserted object to generate a photoacoustic wave and the tip portion of the inserted object is visualized using a photoacoustic image in consideration of the above description.

In order to attain the above-described object, a photoacoustic image-generating apparatus of the invention includes a light source, an inserted object, of which at least a tip portion is inserted into a subject, the inserted object including a light guide member which guides light from the light source, and a light emission unit which is provided in the vicinity of the tip portion and emits light guided by the light guide member, and generating a photoacoustic wave caused by light from the light emission unit using the tip portion, an acoustic wave detection unit that detects the photoacoustic wave from the inserted object in a state where at least the tip of the inserted object is inserted into the subject, a photoacoustic image generation unit that generates a photoacoustic image based on the detected photoacoustic wave, and a light source control unit that controls the amount of light emitted from the light emission unit based on the photoacoustic image. The term "the vicinity of the tip portion" used herein refers to a position where a photoacoustic wave capable of imaging the position of the tip of the inserted object can be generated with accuracy necessary for a puncture operation in the case where the light emission unit is arranged at this position. For example, the vicinity of the tip portion is within a range of 0 mm to 3 mm from the tip to the base of the inserted object. In the following embodiment, the vicinity of the tip portion has the same meaning.

The light source control unit may calculate a set amount of light based on the photoacoustic image by controlling the light source and sets the amount of light emitted from the light emission unit to the set amount of light.

The inserted object may further include a light absorption member which absorbs light from the light emission unit to generate the photoacoustic wave.

The inserted object may be a puncture needle which has a communication lumen, has an opening at the tip, and punctures the subject. In this case, at least one of the light guide member and the light absorption member may constitute an inner needle which seals at least a part of the lumen of the puncture needle.

It is preferable that the inner needle constituted of the light guide member and the light absorption member is detachable from a puncture needle body constituting an outer needle.

The light absorption member may be arranged at a position of the opening of the puncture needle.

The inserted object may be a puncture needle, and the light guide member may constitute an inner needle which seals at least a part of the puncture needle.

The light source control unit may control the light source based on the photoacoustic image generated in a state where at least the tip portion of the inserted object is inserted into the subject.

The light source control unit may control the light source such that a width at which a pixel value of a peak in the photoacoustic image is equal to or greater than a first threshold value and a pixel value around the peak is equal to or greater than a second threshold value is equal to or less than a predetermined width.

Alternatively, the light source control unit may control the light source such that an area of a pixel having a pixel value of a peak in the photoacoustic image equal to or greater than a first threshold value and a pixel value around the peak equal to or greater than a second threshold value is equal to or less than a predetermined area.

At least one of the first threshold value and the second threshold value may be set according to the type of the inserted object inserted into the subject.

The photoacoustic image generation unit may generate the photoacoustic image periodically. In this case, the light source control unit may control the light source at an interval of multiple frames.

The light source control unit may control the amount of light emitted from the light emission unit in the case where the photoacoustic wave from the inserted object is detected.

The light source control unit may control the amount of light emitted from the light emission unit to the amount of light within a range of a maximum permissible exposure to the subject in the case where the photoacoustic wave from the inserted object is not detected. The "maximum permissible exposure" refers to "the level of laser irradiation without giving harmful effects on a human body even if the human body is irradiated with laser in a normal environment" based on a method defined in the safety standards (JIS C 6802) of laser products.

The photoacoustic image-generating apparatus of the invention may further include a contact detection unit that detects whether or not at least one of the acoustic wave detection unit and the inserted object contacts the subject. In this case, the light source control unit may control the light source in the case where the contact detection unit detects contact.

The acoustic wave detection unit may further detect a reflected acoustic wave with respect to an acoustic wave transmitted toward the subject. The photoacoustic image-generating apparatus may further include a reflected acoustic image generation unit that generates a reflected acoustic image based on the reflected acoustic wave. In this case, the photoacoustic image-generating apparatus may further include an image synthesis unit that synthesizes the photoacoustic image and the reflected acoustic image.

The invention provides a light source control method including a step of detecting a photoacoustic wave from an inserted object, of which at least a tip portion is inserted into the subject, in a state where at least the tip of the inserted object is inserted into a subject, the inserted object including a light guide member which guides light from the light source, and a light emission unit which is provided in the vicinity of the tip portion and emits light guided by the light guide member, and generating the photoacoustic wave caused by light from the light emission unit in the tip portion, a step of generating a photoacoustic image based on the detected photoacoustic wave, and a step of controlling the amount of light emitted from the light emission unit based on the photoacoustic image.

In the photoacoustic image-generating apparatus and the light source control method of the invention, light from the light source is guided to the inserted object to generate the photoacoustic wave in the tip portion, the photoacoustic image in which the photoacoustic wave is detected is generated, and the amount of light irradiating the tip portion of the inserted object is controlled based on the photoacoustic image. For example, in the case where the detected photoacoustic wave is weak, the amount of light emitted from the light source is increased, whereby the photoacoustic wave generated in the tip portion of the inserted object is intensified. Conversely, in the case where the detected photoacoustic wave is intense, the amount of light emitted from the light source is decreased, whereby the photoacoustic wave generated in the tip portion of the inserted object is weakened. In this way, even if the inserted object is inserted to a deep position of the subject, the position of the tip of the inserted object can be confirmed using the photoacoustic image. Furthermore, it is possible to suppress the occurrence of a flare-like artifact in the case where the insertion position of the inserted object is shallow, or the occurrence of an artifact due to multiple reflections, and to improve visibility of the tip portion of the inserted object

DESCRIPTION OF THE PREFERRED EMBODIMENTS

Figure 1:
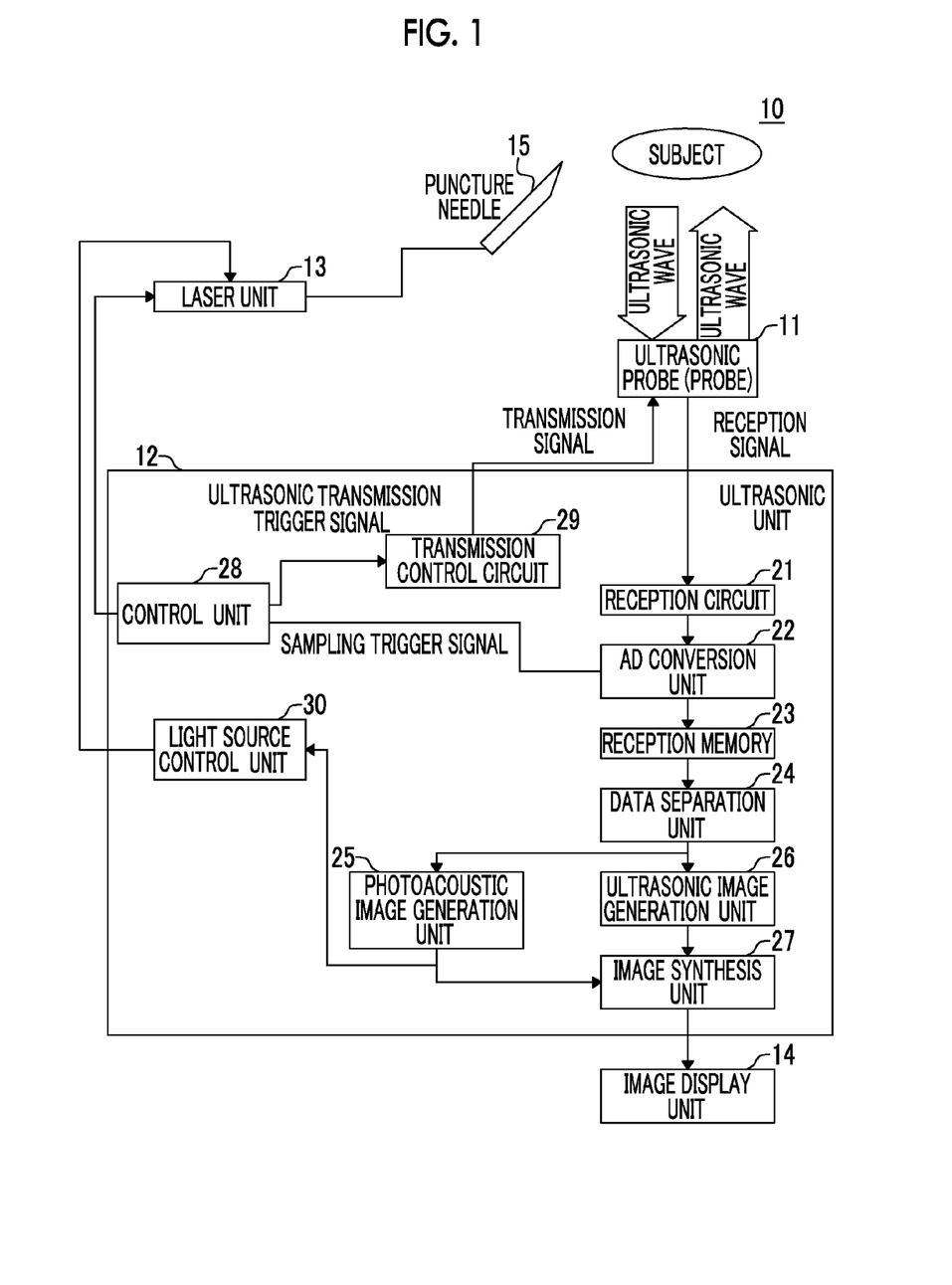
FIG. 1 is a block diagram showing a photoacoustic image-generating apparatus according to an embodiment of the invention.

Hereinafter, an embodiment of the invention will be described in detail referring to the drawings. FIG. 1 shows a photoacoustic image-generating apparatus according to an embodiment of the invention. A photoacoustic image-generating apparatus (photoacoustic image diagnostic apparatus) 10 includes a probe (ultrasonic probe) 11, an ultrasonic unit 12, and a laser unit 13. In the embodiment of the invention, although an ultrasonic wave is used as an acoustic wave, the acoustic wave is not limited to the ultrasonic wave, and an acoustic wave of an audio frequency may be used as long as an appropriate frequency is selected according to an inspection target, measurement conditions, or the like.

The laser unit 13 is a light source which emits light guided to an inserted object, and includes, for example, a laser diode (semiconductor laser). The type of the laser is not particularly limited, and may be, for example, a solid-state laser using yttrium aluminum garnet (YAG), alexandrite, or the like. Alternatively, an optical amplification type laser beam source with a laser diode as a seed light source may be used.

In this embodiment, as the inserted object, of which at least the tip portion is inserted into a subject, a puncture needle which is punctured in the subject is considered. A puncture needle 15 has an opening at the tip, and is formed in a hollow shape. A laser beam emitted from the laser unit 13 is guided to the puncture needle 15, for example, using a light guide member such as an optical fiber.

Figure 2:
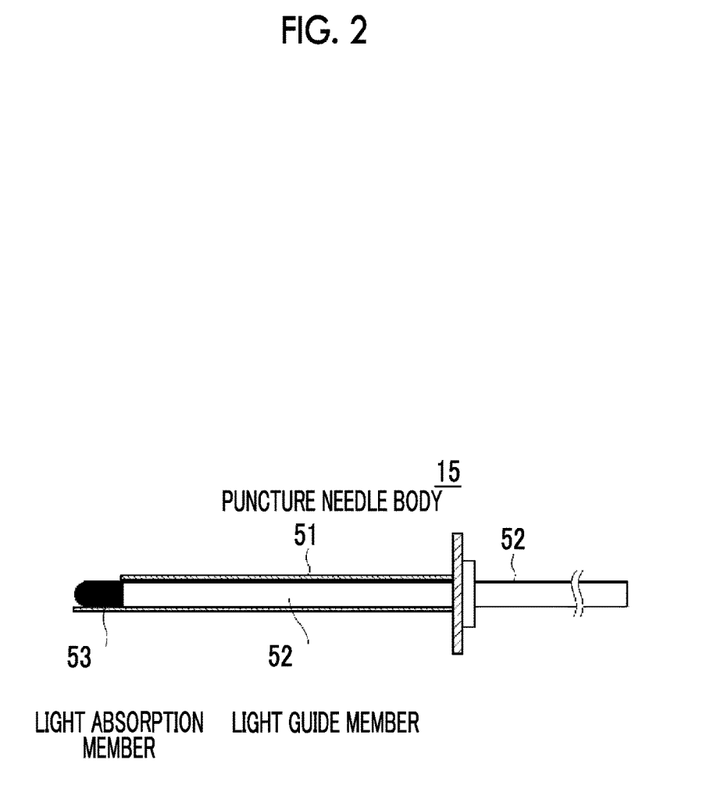
FIG. 2 is a sectional view showing a cross-section of a puncture needle.

FIG. 2 shows a cross-section of the puncture needle 15. The puncture needle 15 has a hollow puncture needle body 51 which has an opening at the tip formed at an acute angle and has a lumen formed inside, a light guide member 52 which guides light from the laser unit 13 to the vicinity of the opening of the puncture needle, and a light absorption member 53 which is provided at a position where the vicinity of the opening is irradiated with light emitted from the light emission unit of the light guide member 52. The light guide member 52 is constituted of, for example, an optical fiber, and the end surface of the optical fiber in the light advancing direction from the laser unit 13 constitutes a light emission unit. For example, a laser beam of 0.2 mJ is emitted from the light emission unit.

The light absorption member 53 absorbs light from the light emission unit of the light guide member 52 to generate a photoacoustic wave. The light absorption member 53 is formed of, for example, silicone rubber in which a black pigment is mixed, or black coating having high light absorption with respect to the wavelength of the laser beam. Alternatively, the light absorption member 53 may be formed of a metal film or a film of oxide having light absorption with respect to the wavelength of the laser beam. For example, as the light absorption member 53, a film of oxide such as iron oxide, chromium oxide, or manganese oxide, having high light absorption with respect to the wavelength of the laser beam may be used. Alternatively, a metal film, such as Ti, Au, or Pt, having lower light absorption than oxide but high biocompatibility may be used as the light absorption member 53.

The light guide member 52 and the light absorption member 53 have the substantially same outer diameter as the inner diameter of the hollow puncture needle body 51. The light guide member 52 and the light absorption member 53 also function as an inner needle which seals at least a part of the lumen of the puncture needle body 51. The lumen of the puncture needle body 51 may be sealed by at least one of the light guide member 52 and the light absorption member 53. The light guide member 52 and the light absorption member 53 are retractable (detachable) from the hollow puncture needle body 51.

An operator punctures the puncture needle 15 into the subject in a state where the light guide member 52 and the light absorption member 53 constituting an inner needle are set into the puncture needle body 51. Since the lumen of the puncture needle body 51 is closed by the inner needle, it is possible to prevent rolling of flesh when puncturing with the needle, and to prevent a sense of puncturing of the operator from being obstructed. Furthermore, it is possible to prevent the entrance of moisture from the punctured region to the lumen of the puncture needle body 51. The operator removes the inner needle from the puncture needle body 51 after being punctured in the subject. After the inner needle is removed, the operator mounts a syringe or the like on an outer needle base (not shown) and for example, performs injection of a medicine, such as an anesthetic. Alternatively, a biopsy tissue sample is gathered from a part of the subject where the puncture needle 15 is punctured.

In FIG. 2, although the puncture needle has the light absorption member 53, the light absorption member 53 may not necessarily be provided. Instead of using the light absorption member 53, the inner wall of the puncture needle body 51 is irradiated with light from the light guide member 52 to generate the photoacoustic wave at the portion of the tip of the needle. The light guide member 52 and the light absorption member 53 may not necessarily constitute the inner needle, and the outer diameter of the light guide member 52 and the light absorption member 53 may be smaller than the inner diameter of the lumen of the puncture needle body 51.

Returning to FIG. 1, the probe 11 is an acoustic wave detection unit, and for example, has a plurality of ultrasonic transducers arranged in a one-dimensional manner. The probe 11 detects the photoacoustic wave generated due to light emitted from the light emission unit of the light guide member 52 (FIG. 2) in a state where the puncture needle 15 is punctured in the subject. The probe 11 performs transmission of an acoustic wave (ultrasonic wave) to the subject and reception of a reflected acoustic wave (reflected ultrasonic wave) from the subject with respect to the transmitted ultrasonic wave, in addition to detection of the photoacoustic wave.

The ultrasonic unit 12 has a reception circuit 21, a AD conversion unit 22, a reception memory 23, a data separation unit 24, a photoacoustic image generation unit 25, an ultrasonic image generation unit 26, an image synthesis unit 27, a control unit 28, a transmission control circuit 29, and a light source control unit 30. The reception circuit 21 receives a detection signal of the photoacoustic wave detected by the probe 11. The reception circuit 21 also receives a detection signal of the reflected ultrasonic wave detected by the probe 11.

The AD conversion unit 22 converts the detection signals of the photoacoustic wave and the reflected ultrasonic wave received by the reception circuit 21 to digital signals. For example, the AD conversion unit 22 samples the detection signals of the photoacoustic wave and the reflected ultrasonic wave in a predetermined sampling period based on a sampling clock signal of a predetermined period. The AD conversion unit 22 stores the sampled detection signal (sampling data) of the photoacoustic wave and the reflected ultrasonic wave in the reception memory 23.

The data separation unit 24 separates sampling data of the detection signal of the photoacoustic wave from sampling data of the detection signal of the reflected ultrasonic wave which are stored in the reception memory 23. The data separation unit 24 inputs sampling data of the detection signal of the photoacoustic wave to the photoacoustic image generation unit 25. The data separation unit 24 also inputs separated sampling data of the reflected ultrasonic wave to the ultrasonic image generation unit (a reflected acoustic image generation unit) 26.

The photoacoustic image generation unit 25 generates a photoacoustic image based on the detection signal of the photoacoustic wave detected by the probe 11. The generation of the photoacoustic image includes, for example, image reconstruction, such as phase matching and addition, detection, logarithmic conversion, and the like. The ultrasonic image generation unit 26 generates an ultrasonic image (reflected acoustic image) based on the detection signal of the reflected ultrasonic wave detected by the probe 11. The generation of the ultrasonic image also includes, image reconstruction, such as phase matching and addition, detection, arithmetic conversion, and the like. For example, the photoacoustic image generation unit 25 and the ultrasonic image generation unit 26 generate the photoacoustic image and the ultrasonic image periodically.

The image synthesis unit 27 synthesizes the photoacoustic image and the ultrasonic image. For example, the image synthesis unit 27 performs image synthesis by superimposing the photoacoustic image on the ultrasonic image. A synthesized image is displayed on an image display unit 14, such as a display. Without performing image synthesis, The photoacoustic image and the ultrasonic image may be displayed next to each other on the image display unit 14, or the photoacoustic image and the ultrasonic image may be displayed alternately.

The control unit 28 controls the respective units in the ultrasonic unit 12. For example, the control unit 28 sends a trigger signal to the laser unit 13, and causes a laser beam to be emitted from the laser unit 13. The control unit 28 also sends a sampling trigger signal to the AD conversion unit 22 with the irradiation of the laser beam, and controls the sampling start timing of the photoacoustic wave.

When generating the ultrasonic image, the control unit 28 sends an ultrasonic transmission trigger signal to the transmission control circuit 29 to perform ultrasonic wave transmission. If the transmission control circuit 29 receives the ultrasonic transmission trigger signal, the transmission control circuit 29 causes an ultrasonic wave to be transmitted from the probe 11. The control unit 28 sends a sampling trigger signal to the AD conversion unit 22 in response to the timing of ultrasonic transmission, and makes the AD conversion unit 28 start the sampling of the reflected ultrasonic wave.

The light source control unit 30 controls the amount of light emitted from the light emission unit of the light guide member 52 based on the photoacoustic image generated by the photoacoustic image generation unit 25. The light source control unit 30 controls the laser unit 13 based on the photoacoustic image generated after at least the tip portion of the puncture needle 15 is inserted into the subject. It is preferable that the light source control unit 30 does not perform the control of the laser unit 13 when the photoacoustic wave from the puncture needle 15 is not detected. It is possible to determine whether or not the photoacoustic wave from the puncture needle 15 is detected based on the pixel value of the photoacoustic image.

For example, the light source control unit 30 calculates a set amount of light based on the photoacoustic image, and controls the laser unit 13 such that the amount of light emitted from the light emission unit becomes the set amount of light. The light source control unit 30 may calculate the set amount of light each time when the photoacoustic image generation unit 25 generates the photoacoustic image, or may calculate the set amount of light at an interval of multiple frames. In the case that the set amount of light is calculated at an interval of multiple frames, the photoacoustic images of multiple frames are added and averaged, and the set amount of light can be calculated based on the added and averaged photoacoustic image.

Figure 3:
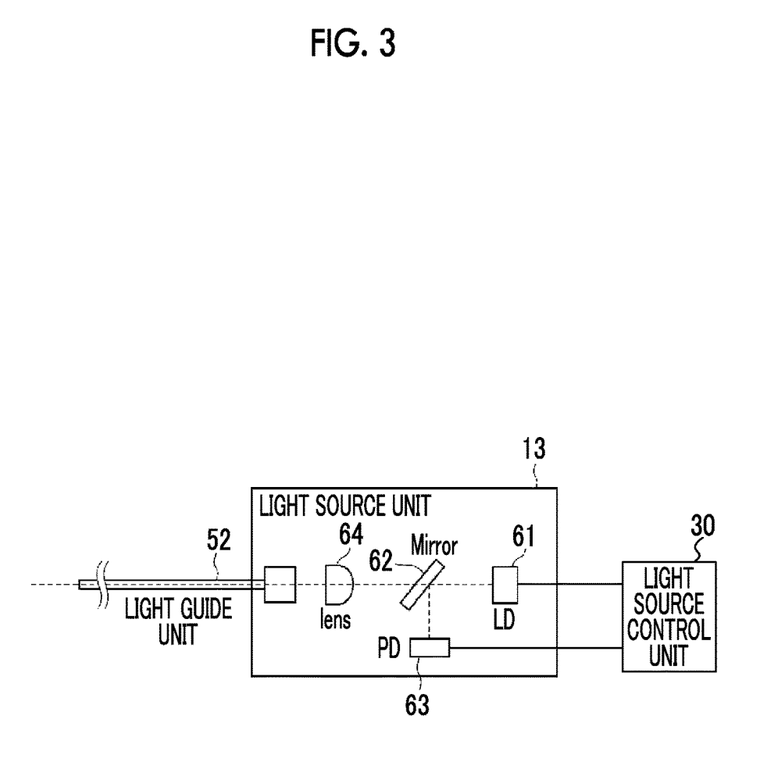
FIG. 3 is a block diagram showing the configuration of a laser unit.

FIG. 3 shows the configuration of the laser unit 13. The laser unit 13 has a laser diode 61, a mirror 62, a photodetector 63, and a lens 64. The light source control unit 30 drives the laser diode 61. The mirror 62 reflects a part of light emitted from the laser diode 61 toward the photodetector 63, and transmits the rest of light. Light transmitted through the mirror 62 is incident on the light guide member 52 through the lens 64.

The photodetector 63 receives light reflected in the mirror 62, and outputs a signal according to the amount of incident light. The light source control unit 30 controls the output of the laser diode 61 based on the output signal of the photodetector 63. For example, the light source control unit 30 controls the output of the laser diode 61 such that the output signal of the photodetector 63 has the magnitude of a signal corresponding to the set amount of light. Instead of controlling the output of the laser diode 61, the amount of light emitted from the light emission unit may be controlled by attenuating the light in an optical path to the light emission unit of the light guide member 52.

If the light irradiating the light absorption member 53 (FIG. 2) in the puncture needle 15 is intense, the photoacoustic wave generated at the tip is intensified, the portion of the tip of the needle in the photoacoustic image is expressed in a thick form, and the position of the tip of the needle is hardly recognized visually. When a photoacoustic image is displayed on the background of an ultrasonic image, the background ultrasonic image is hidden due to the extended photoacoustic wave, the positional relationship between the tip of the puncture needle and a blood vessel to be punctured is difficult to recognize, and accurate puncturing is obstructed. The light source control unit 30 may control the amount of light emitted from the laser unit 13 such that the tip of the needle is equal to or less than given thickness in the photoacoustic image.

For example, the light source control unit 30 controls the laser unit 13 based on the distribution of a pixel value in the photoacoustic image. The light source control unit 30 controls the laser unit 13 such that a width at which a pixel value of a peak in the photoacoustic image is equal to or greater than a first threshold value and a pixel value around the peak is equal to or greater than a second threshold value is equal to or less than a predetermined width (m, pixel, or the like). The first threshold value corresponds to a lower limit value of a signal of a portion where a photoacoustic wave (photoacoustic signal) exists, and the second threshold value corresponds to a lower limit value of a signal of a portion, the portion of the photoacoustic image being displayed brightly.

Figure 4:
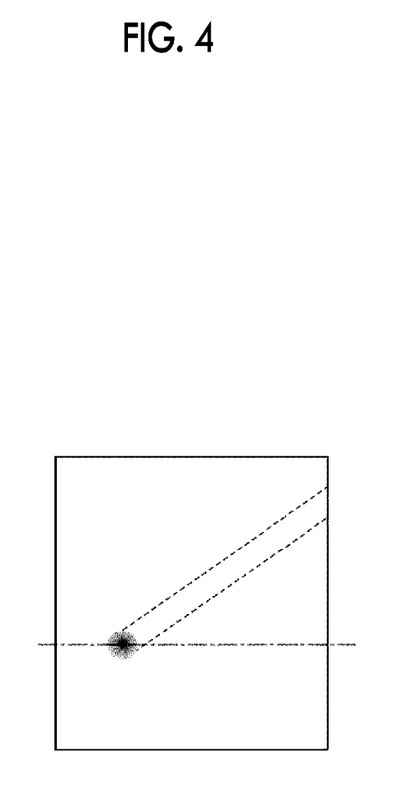
FIG. 4 is a diagram showing a photoacoustic image.

FIG. 4 shows a photoacoustic image. A portion of a tip of a needle portion in a photoacoustic image is displayed brightly due to a photoacoustic wave from the light absorption member 53 which exists at the tip of the needle. For example, the light source control unit 30 extracts a photoacoustic image from this photoacoustic image in a direction orthogonal to a depth direction, determines the width of a bright portion based on the distribution of the extracted photoacoustic image, and controls the output of the laser diode 61 such that the width does not exceed a predetermined length.

Figure 5:
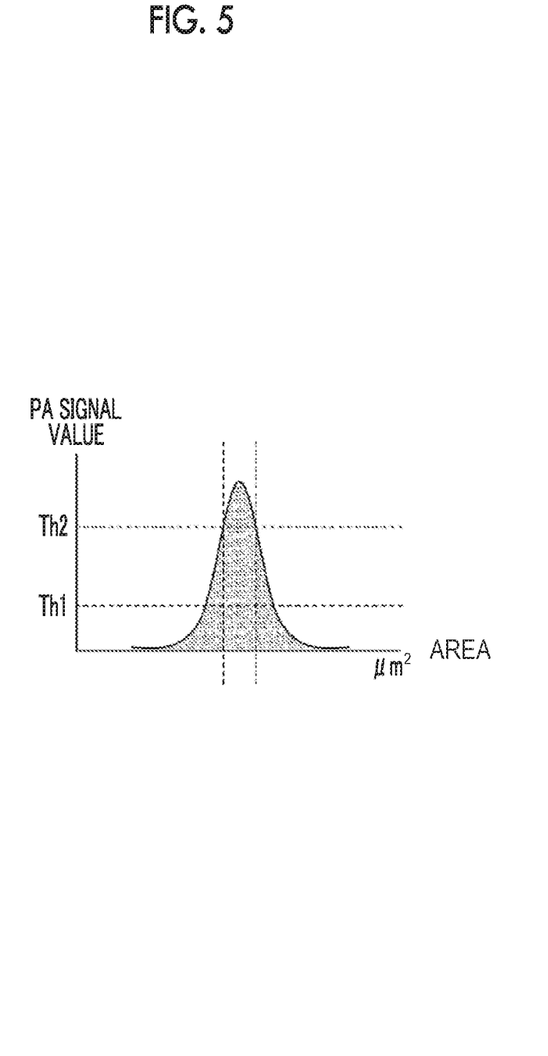
FIG. 5 is a graph showing the distribution of a pixel value of a photoacoustic image.

FIG. 5 shows the distribution of a pixel value of a photoacoustic image. The pixel values of the photoacoustic image are associated with the intensity of the photoacoustic wave generated at the tip portion of the puncture needle 15. The light source control unit 30 refers to a pixel having a pixel value equal to or greater than a first threshold value Th1 as a pixel where the a photoacoustic wave is detected. The light source control unit 30 determines a width w for the pixel where the photoacoustic wave is detected such that the pixel value is equal to or greater than a second threshold value Th2 corresponding to predetermined brightness. If the width w is greater than a predetermined width, for example, 100 the set amount of light is made lower than the current set amount of light such that the width w is equal to or less than the predetermined width. The output of the laser diode 61 is lowered so as to become the updated set amount of light, whereby the photoacoustic wave generated in the light absorption member 53 is weakened, and the width w at which the pixel value is equal to or greater than the second threshold value Th2 is narrowed.

Alternatively, the laser unit 13 may be controlled based on an area of a portion in the photoacoustic image corresponding to the photoacoustic wave from the tip of the needle. In this case, for example, the light source control unit 30 may control the laser unit 13 such that an area of a pixel having a pixel value of a peak in the photoacoustic image equal to or greater than the first threshold value and a pixel value around the peak equal to or greater than the second threshold value is equal to or less than a predetermined area ($\mu m^2$, $pixel^2$, or the like).

Figure 6:
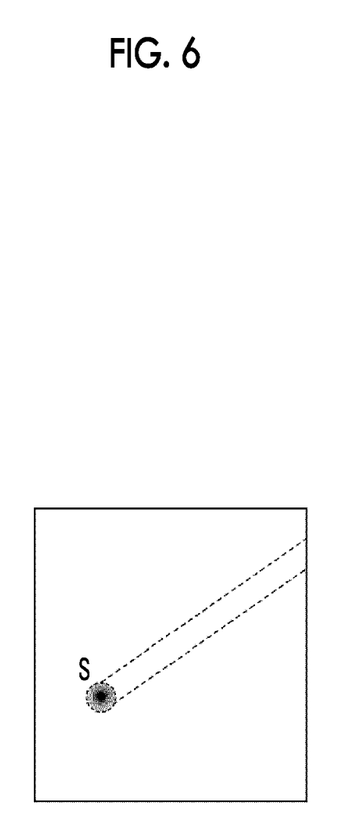
FIG. 6 is a diagram showing a photoacoustic image.

FIG. 6 shows a photoacoustic image. Similar to FIG. 4, the portion of the tip of the needle in the photoacoustic image is displayed brightly due to the photoacoustic wave from the light absorption member 53 which exists at the tip of the needle. The light source control unit 30 determines a pixel in the photoacoustic image where the photoacoustic wave is detected, and determines an area S of a bright portion for this pixel. The light source control unit 30 controls the output of the laser diode 61 such that the area S is equal to or less than a predetermined area, for example, 10000 $\mu m^2$.

Figure 7:
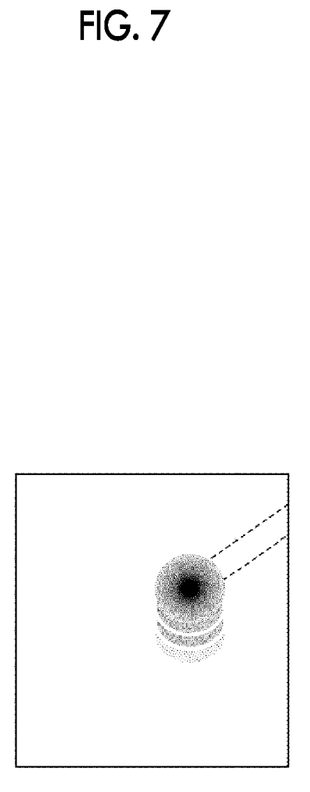
FIG. 7 is a diagram showing a photoacoustic image in which an artifact occurs.

FIG. 7 shows a photoacoustic image where an artifact occurs. The distribution of a portion where the photoacoustic wave is detected is not limited to the case of being expanded like a circular shape. For example, when the photoacoustic wave generated in the light absorption member 53 is reflected in the puncture needle body 51 multiple times, the artifact occurs downward from the needle, and accurate puncturing is obstructed. In this case, the light source control unit 30 lowers the output of the laser diode 61 based on the photoacoustic image according to the above-described method, whereby the artifact can be reduced.

Incidentally, even if the amount of light emitted from the laser unit 13 is constant, the intensity of the photoacoustic wave generated in the light absorption member 53 may change depending on the thickness of the puncture needle to be punctured or the material of the light absorption member 53. At least one of the first threshold value and the second threshold value may be set according to the type of the puncture needle inserted into the subject. The predetermined width when the laser unit 13 is controlled based on the width of the pixel having the pixel value equal to or greater than the second threshold value Th2 and the predetermined area when the laser unit 13 is controlled based on the area of the pixel having the pixel value equal to or greater than the second threshold value Th2 may be set according to the type of the puncture needle. For example, parameters such as the first threshold value Th1, the second threshold value Th2, the predetermined width or the predetermined area, and the like, may be stored in a table in association with the type of the puncture needle, and a parameter corresponding to a puncture needle to be used may be acquired with reference to the table.

Figure 8:
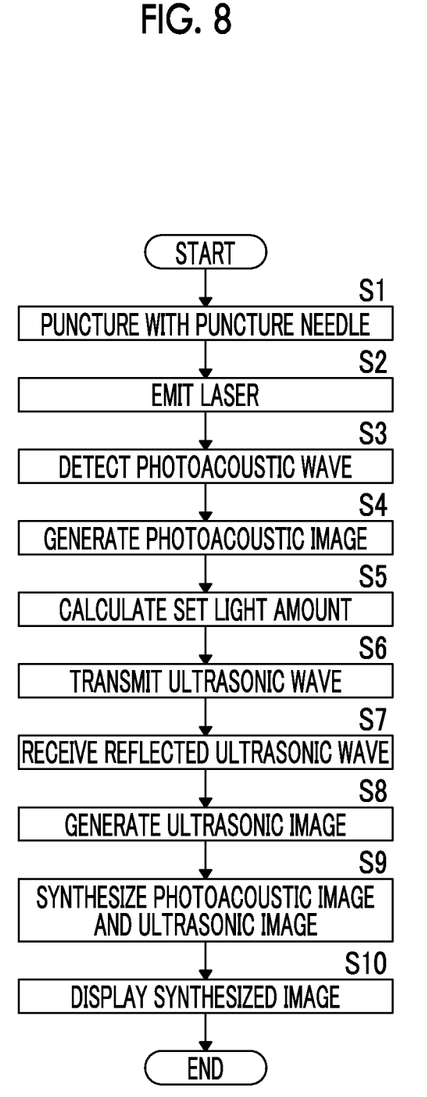
FIG. 8 is a flowchart showing an operation procedure.

FIG. 8 shows an operation procedure. The puncture needle 15 is punctured in the subject by a physician or the like (Step S1). After the puncture needle 15 is punctured, the control unit 28 of the ultrasonic unit 12 sends a trigger signal to the laser unit 13. If the trigger signal is received, the laser unit 13 emits a pulsed laser beam. The pulsed laser beam emitted from the laser unit 13 is guided to the vicinity of the tip of the puncture needle 15 by the light guide member 52 (FIG. 2), and is emitted from the light emission unit to the light absorption member 53 (Step S2).

The probe 11 detects a photoacoustic wave generated due to the absorption of the laser beam by the absorption member 53 (Step S3). The AD conversion unit 22 receives a detection signal of the photoacoustic wave through the reception circuit 21, samples the detection signal of the photoacoustic wave, and stores the detection signal in the reception memory 23. The data separation unit 24 sends the detection signal of the photoacoustic wave stored in the reception memory 23 to the photoacoustic image generation unit 25. The photoacoustic image generation unit 25 generates a photoacoustic image based on the detection signal of the photoacoustic wave (Step S4).

The light source control unit 30 calculates the set amount of light of the laser unit 13 based on the photoacoustic image generated in Step S4 (Step S5). The light source control unit 30 controls the laser unit 13 such that the amount of light emitted from the laser diode 61 (FIG. 3) becomes the set amount of light at the time of next laser emission. The photoacoustic image referred to by the light source control unit 30 may be at least a reconstructed photoacoustic image, and may not necessarily be a photoacoustic image for display which is displayed on a display or the like.

The light source control unit 30 may execute Step S5 only when the photoacoustic wave is detected in Step S3, and may control the laser unit 13. For example, in the case that the photoacoustic wave is not detected in Step S3, the case being for example that the tip portion of the puncture needle 15 is out of the range where an acoustic wave is detectable in the probe 11, Step S5 may not be executed, and the amount of light emitted from the laser unit 13 may not be changed. Alternatively, when the photoacoustic wave is undetectable, a maximum light amount set in a range without causing problems on the living body may be set as the set amount of light.

The control unit 28 sends an ultrasonic transmission trigger signal to the transmission control circuit 29. The transmission control circuit 29 causes an ultrasonic wave to be transmitted from the probe 11 in response to the ultrasonic transmission trigger signal (Step S6). After the ultrasonic wave is transmitted, the probe 11 detects a reflected ultrasonic wave from the subject (Step S7). Transmission and reception of the ultrasonic wave may be separated. For example, transmission of an ultrasonic wave may be performed from a position different from the probe 11, and a reflected ultrasonic wave to the transmitted ultrasonic wave may be received by the probe 11.

The reflected ultrasonic wave detected by the probe 11 is input to the AD conversion unit 22 through the reception circuit 21. The AD conversion unit 22 stores sampling data of the reflected ultrasonic wave in the reception memory 23.

The data separation unit 24 sends the detection signal of the reflected ultrasonic wave stored in the reception memory 23 to the ultrasonic image generation unit 26. The ultrasonic image generation unit 26 generates an ultrasonic image based on the detection signal of the reflected ultrasonic wave (Step S8). The image synthesis unit 27 synthesizes the photoacoustic image generated in Step S4 and the ultrasonic image generated in the Step S7 (Step S9). An image synthesized in Step S9 is displayed on the image display unit 14 (Step S10).

In this embodiment, light from the laser unit 13 is guided to the tip of the puncture needle 15, and the photoacoustic wave is generated in the tip portion of the puncture needle 15. The light source control unit 30 controls the laser unit 13 based on the photoacoustic image based on the detected photoacoustic wave. The light source control unit 30 controls the amount of light guided to the tip of the puncture needle 15 based on the detected photoacoustic wave, whereby it is possible to guide an appropriate amount of light to the tip portion of the puncture needle 15 according to the position of the puncture needle 15, and to control the intensity of the photoacoustic wave generated in the tip portion to appropriate intensity. For example, in the case that puncturing is shallow, the amount of light emitted from the laser unit 13 is decreased, whereby it is possible to suppress an artifact due to excessively intense photoacoustic waves from the tip portion of the puncture needle 15. Conversely, in the case that puncturing is deep, the amount of light emitted from the laser unit 13 is increased, whereby a photoacoustic wave of sufficient intensity can be generated from the tip portion at a deep position. In this way, visibility of the tip of the needle can be improved and accurate puncturing can be assisted.

JP2008-253482A describes that light is irradiated toward a photoacoustic wave generation unit, that it is determined whether or not a photoacoustic signal from the photoacoustic wave generation unit has appropriate magnitude, and that an amplification factor of an amplifier or the amount of light of a light source is changed according to the result. However, in JP2008-253482A, the irradiation of the light to the photoacoustic wave generation unit is performed in a period during which a measurement is not performed on a living body, and in JP2008-253482A, a configuration in which the amount of light from the light source is controlled according to the photoacoustic wave from the tip of the punctured needle is not employed. An object of JP2008-253482A is to detect deterioration or failure of an acoustic wave detection unit, and hence the distance between the photoacoustic wave generation unit and the acoustic wave detection unit is constant. Accordingly, in JP2008-253482A, the photoacoustic wave generation unit cannot be arranged at the tip of the puncture needle which is punctured in the subject.

In the foregoing embodiment, although light irradiation to the tip portion of the puncture needle 15 has been described, in addition to this, light irradiation from the surface of the subject may be performed separately, and a photoacoustic wave generated due to light irradiation may be detected to generate a photoacoustic image. In this case, a photoacoustic image obtained by imaging the photoacoustic wave generated with light irradiation to the tip portion of the puncture needle 15 and a photoacoustic image obtained by imaging the photoacoustic wave due to light irradiation from the surface of the subject may be displayed in a superimposed manner.

The puncture needle is not limited to a puncture needle which is punctured in the subject from the outside of the subject percutaneously, and may be a needle for an ultrasonic endoscope. In the foregoing embodiment, although the puncture needle has been considered as the inserted object, the invention is not limited thereto. The inserted object may be a needle for radiofrequency ablation which internally accommodates an electrode for use in radiofrequency ablation, may be a catheter which is inserted into a blood vessel, or may be a guide wire of a catheter which is inserted into a blood vessel. Alternatively, an optical fiber for laser treatment may be used.

Figure 9:
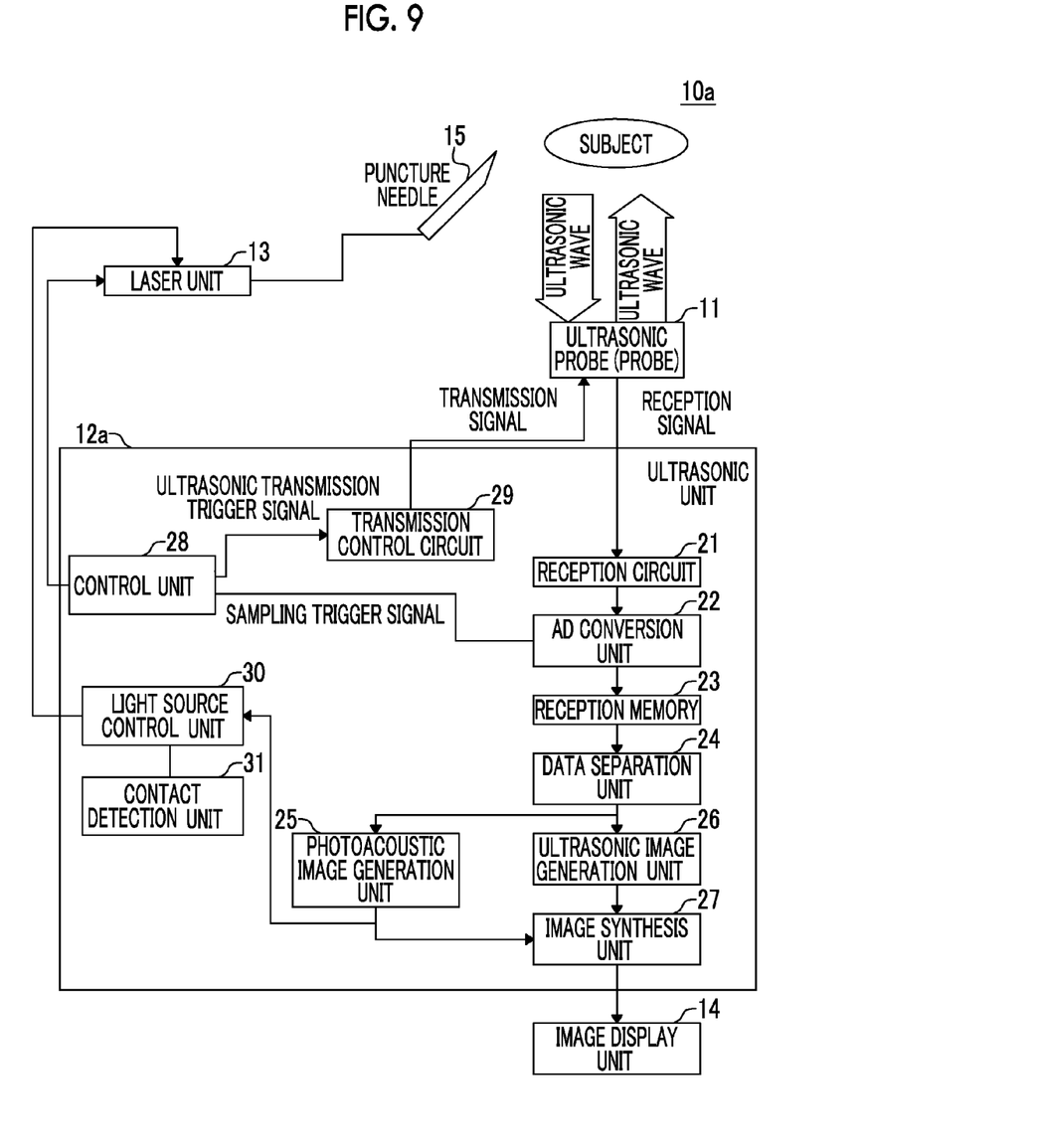
FIG. 9 is a block diagram showing a photoacoustic image-generating apparatus of a modification example.

FIG. 9 shows a photoacoustic image-generating apparatus of a modification example. A photoacoustic image-generating apparatus 10a of the modification example further includes a contact detection unit 31 in an ultrasonic unit 12a. The contact detection unit 31 detects that at least one of the probe 11 and the puncture needle 15 contacts the subject. For example, the contact detection unit 31 detects contact with the subject using a pressure sensor or the like. Alternatively, the spatial position of the probe 11 or the puncture needle 15 is recognized using a magnetic sensor or the like, and contact with the subject may be detected based on the positional information. The light source control unit 30 performs the control of the laser unit 13 when contact with the contact detection unit 31 is detected. In this way, when the probe 11 does not come into contact with the subject and thus the detection of the photoacoustic wave is not performed, or when the puncture needle 15 is not punctured in the subject and thus the photoacoustic wave from the tip of the needle is undetectable by the probe 11, it is possible to prevent an intense laser beam from being emitted from the laser unit 13.

Although the invention has been described based on the preferred embodiment has been described, the photoacoustic image-generating apparatus and the light source control method of the invention are not limited to only the foregoing embodiment, and various corrections and alterations from the configuration of the foregoing embodiment still fall within the range of the invention.

EXPLANATION OF REFERENCES

10: photoacoustic image-generating apparatus
11: probe
12: ultrasonic unit
13: laser unit
14: image display unit
15: puncture needle
21: reception circuit
22: AD conversion unit
23: reception memory
24: data separation unit
25: photoacoustic image generation unit
26: ultrasonic image generation unit
27: image synthesis unit
28: control unit
29: transmission control circuit
30: light source control unit
31: contact detection unit
51: puncture needle body
52: light guide member
53: light absorption member 61: laser diode
62: mirror
63: photodetector
64: lens

What is claimed is:

1. A photoacoustic image-generating apparatus comprising:
   a light source;
   an inserted object, of which at least a tip portion is adapted to be inserted into a subject, the inserted object including a light guide member which guides light from the light source, and an end surface of the light guide member in light advancing direction from the light source that is provided in a vicinity of the tip portion and emits the light guided by the light guide member, and generating a photoacoustic wave caused by the light from the end surface of the light guide member in the light advancing direction from the light source in the tip portion;
   a probe that detects the photoacoustic wave from the inserted object in a state where at least the tip of the inserted object is inserted into the subject; and
   a processor, the processor configured to
      generate a photoacoustic image based on the detected photoacoustic wave,
      analyze the photoacoustic image to determine pixel values in the photoacoustic image, where the analysis comprises
         generating a distribution graph of the pixel values in the photoacoustic image; and
         based on the distribution graph, determining an area of a pixel having a pixel value of a peak in the photoacoustic image equal to or greater than a first threshold value and a pixel value around the peak equal to or greater than a second threshold value; and
      control an updated set amount of light emitted from the end surface of the light guide member in the light advancing direction from the light source based on the the determined area,
         wherein the updated set amount of light is controlled such that the determined area is equal to or less than a predetermined area.

2. The photoacoustic image-generating apparatus according to claim 1, wherein the inserted object further includes a light absorption member which absorbs light from the end surface of the light guide member in the light advancing direction from the light source to generate the photoacoustic wave.

3. The photoacoustic image-generating apparatus according to claim 1, wherein the inserted object further includes a light absorption member which absorbs light from the end surface of the light guide member in the light advancing direction from the light source unit to generate the photoacoustic wave.

4. The photoacoustic image-generating apparatus according to claim 2,
   wherein the inserted object is a puncture needle which has a communication lumen, has an opening at the tip, and punctures the subject, and
   at least one of the light guide member and the light absorption member becomes an inner needle which seals at least a part of the lumen of the puncture needle.

5. The photoacoustic image-generating apparatus according to claim 3,
   wherein the inserted object is a puncture needle which has a communication lumen, has an opening at the tip, and punctures the subject, and
   at least one of the light guide member and the light absorption member becomes an inner needle which seals at least a part of the lumen of the puncture needle.

6. The photoacoustic image-generating apparatus according to claim 4,
   wherein the inner needle is detachable from the body of the puncture needle constituting an outer needle.

7. The photoacoustic image-generating apparatus according to claim 4,
   wherein the light absorption member is positioned in the opening of the puncture needle.

8. The photoacoustic image-generating apparatus according to claim 1,
   wherein the inserted object is a puncture needle which has a communicating lumen, has an opening at the tip, and punctures the subject, and
   the light guide member becomes an inner needle which seals at least a part of the lumen of the puncture needle.

9. The photoacoustic image-generating apparatus according to claim 1,
   wherein the processor further configured to control the light source based on the photoacoustic image generated in a state where at least the tip portion of the inserted object adapted to be inserted into the subject.

10. The photoacoustic image-generating apparatus according to claim 1, wherein at least one of the first threshold value and the second threshold value is set according to a type of the inserted object inserted into the subject.

11. The photoacoustic image-generating apparatus according to claim 1,
    wherein the processor further configured to generate the photoacoustic image periodically, and control the light source at an interval of multiple frames.

12. The photoacoustic image-generating apparatus according to claim 1, wherein the processor further configured to control the updated set amount of light emitted from the end surface of the light guide member in the light advancing direction from the light source in the case where the photoacoustic wave from the inserted object is detected.

13. The photoacoustic image-generating apparatus according to claim 1, wherein the processor further configured to control the updated set amount of light emitted from the end surface of the light guide member in the light advancing direction from the light source to the amount of light within a range of a maximum permissible exposure to the subject in the case where the photoacoustic wave from the inserted object is not detected.

14. The photoacoustic image-generating apparatus according to claim 1, further comprising:
    the processor further configured to detect whether or not at least one of the probe and the inserted object contacts the subject, and
    control the light source in the case where at least one of the probe and the inserted object contacts the subject.

15. The photoacoustic image-generating apparatus according to claim 1,
    wherein the probe further detects a reflected acoustic wave with respect to an acoustic wave transmitted toward the subject, and
    the photoacoustic image-generating apparatus further comprises:
    a reflected acoustic image generation unit that generates a reflected acoustic image based on the reflected acoustic wave.

16. The photoacoustic image-generating apparatus according to claim 15, further comprising:
   the processor further configured to synthesize the photoacoustic image and the reflected acoustic image.

17. A light source control method using in photoacoustic image-generating apparatus according to claim 1 comprising:
   a step of controlling the probe for detecting the photoacoustic wave from an inserted object, of which at least the tip portion is adapted to be inserted into the subject, in a state where at least the tip of the inserted object adapted to be inserted into the subject, the inserted object including the light guide member which guides the light from the light source, and the end surface of the light guide member in the light advancing direction from the light source which is provided in the vicinity of the tip portion and emits the light guided by the light guide member, and generating the photoacoustic wave caused by the light from the end surface of the light guide member in the light advancing direction from the light source in the tip portion;
   a step of controlling the processor to perform the generation of the photoacoustic image based on the detected photoacoustic wave; and
   a step of controlling the processor to perform the analysis of the photoacoustic image to determine pixel values in the photoacoustic image,
   a step of controlling the processor to perform the control of the updated set amount of light emitted from the end surface of the light guide member in the light advancing direction from the light source based on the photoacoustic image that was analyzed.

* * * * *